United States Patent [19]

Adelstein et al.

[11] 4,066,654

[45] Jan. 3, 1978

[54] 1-TRIARYLALKYL-4-PHENYL-4-PIPERIDINE CARBOXYLIC ACIDS AND DERIVATIVES

[75] Inventors: Gilbert W. Adelstein, Evanston; Esam Z. Dajani, Buffalo Grove; Chung Hwai Yen, Skokie, all of Ill.

[73] Assignee: G. D. Searle & Co., Chicago, Ill.

[21] Appl. No.: 741,589

[22] Filed: Nov. 15, 1976

Related U.S. Application Data

[63] Continuation-in-part of Ser. No. 568,439, April 16, 1975, Pat. No. 3,998,832.

[51] Int. Cl.$^2$ .................. C07D 401/06; C07D 211/64
[52] U.S. Cl. .................. 260/293.69; 260/293.72; 260/293.81; 424/267; 424/263
[58] Field of Search .................. 260/293.69, 293.72, 260/293.81

[56] References Cited

FOREIGN PATENT DOCUMENTS 691,644  6/1967  Belgium .................. 260/293.57

OTHER PUBLICATIONS

Patai, "J. Chem. Soc.", pp. 716–723, (1962).
Martensson et al., "Acta Chem. Scand", vol. 19, No. 3, pp. 711–722, (1965).
Bochow, "Chem. Ber.", pp. 3475–3482, (1975), vol. 108.

Primary Examiner—Natalie Trousof
Assistant Examiner—Robert T. Bond

Attorney, Agent, or Firm—John J. McDonnell

[57] ABSTRACT

The present invention encompasses compounds of the formula

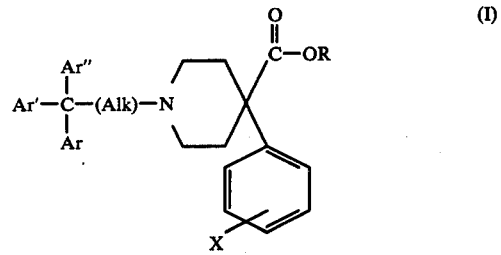

wherein the Alk is straight or branched chain alkylene containing 2–4 carbon atoms; Ar and Ar' are phenyl, Alkyl substituted phenyl wherein the alkyl contains from 1–4 carbon atoms or halo substituted phenyl; Ar" is phenyl, alkyl substituted phenyl wherein the alkyl contains 1–4 carbon atoms, halo substituted phenyl or pyridyl; X is hydrogen, halogen, trifluoromethyl or alkyl having from 1–4 carbon atoms; R is hydrogen, alkyl having from 1–7 carbon atoms, alkenyl having 3–7 carbon atoms, Ar" as herein before defined, or a cation selected from the group consisting of sodium, potassium, ammonium or calcium/2. Compounds of the present invention are potent antidiarrheal agents with little, if any, central nervous system activity.

13 Claims, No Drawings

1-TRIARYLALKYL-4-PHENYL-4-PIPERIDINE CARBOXYLIC ACIDS AND DERIVATIVES

This is a continuation-in-part of our copending application Ser. No. 568,439, filed Apr. 16, 1975, now U.S. Pat. No. 3,998,832.

The present invention encompasses compounds of the formula

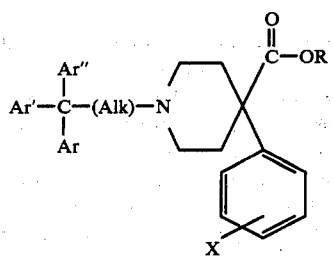

(I)

wherein the Alk is straight or branched chain alkylene containing 2–4 carbon atoms; Ar and Ar' are phenyl, alkyl substituted phenyl wherein the alkyl contains from 1–4 carbon atoms or halo substituted phenyl; Ar'' is phenyl, alkyl substituted phenyl wherein the alkyl contains 1–4 carbon atoms, halo substituted phenyl or pyridyl; X is hydrogen, halogen, trifluoromethyl or alkyl having from 1–4 carbon atoms; R is hydrogen, alkyl having from 1–7 carbon atoms, alkenyl having 3–7 carbon atoms; Ar'' as herein before defined, or a cation selected from the group consisting of sodium, potassium, ammonium or calcium/2.

R represents hydrogen; Alkyl having 1–7 carbon atoms such as methyl, ethyl, propyl, butyl, pentyl, hexyl, heptyl, and the branched chain isomers thereof, 2,3,4-pyridyl phenyl, tolyl, ethylphenyl, butylphenyl, chlorophenyl, fluorophenyl, bromophenyl; alkenyl radicals having the formula Cn—H(2n-1) wherein n is 3–7 carbon atoms such as allyl or methylallyl are suitable allyl radicals. R also represents alkali metal or alkaline earth metal salts such as sodium, potassium, calcium/2, as well as ammonium. Those skilled in the pharmaceutical arts will recognize equivalence of the enumerated metals with other non-toxic pharmaceutically acceptable metal ions. X represents halogen including fluoro, chloro, bromo, iodo; alkyl exemplified by methyl, ethyl, propyl, butyl and the branched chain isomers thereof; or trifluoromethyl.

Ar and Ar' represent phenyl substituted phenyl radicals such as tolyl, ethylphenyl, butylphenyl, chlorophenyl, fluorophenyl, and bromophenyl.

Ar'' represents 2, 3, and 4 pyridyl in addition to phenyl and above exemplified substituted phenyl radicals.

The present invention also includes optically active compounds prepared by resolving the above compounds which have assymetric centers.

The embodiments wherein Alk is —CH₂—CH₂— are particularly preferred.

Compounds of the formula

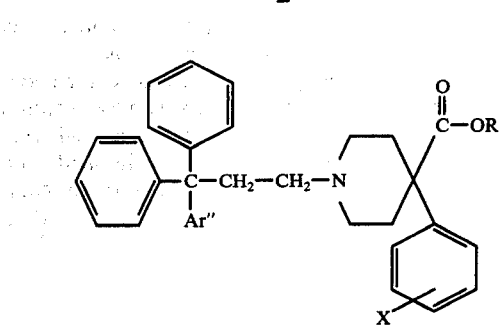

wherein Ar'' is phenyl or pyridyl and X and R are as previously defined are likewise preferred.

The triphenyl derivatives of the formula

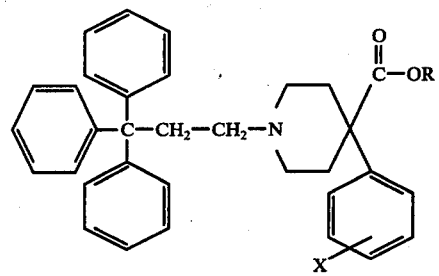

and pyridyl compounds of the formula

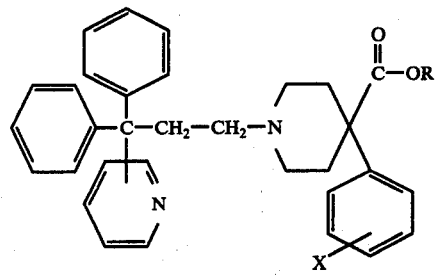

wherein R and X are as earlier defined.

Preferred embodiments are 1-(3,3,3-triphenylpropyl)-4-phenyl-4-piperidinecarboxylic acid and the hydrochloride salts thereof; sodium 1-(3,3,3-triphenylpropyl)-4-phenyl-4-piperidinecarboxylate; potassium 1-(3,3,3-triphenylpropyl)-4-phenyl-4-piperidinecarboxylate; ammonium 1-(3,3,3-triphenylpropyl)-4-phenyl-4-piperidinecarboxylate; ethyl 1-(3,3,3-triphenylpropyl)-4-phenyl-4-piperidinecarboxylate; and the hydrochloride salts thereof; 1-[3,3-diphenyl-3-(2-pyridyl)propyl]-4-phenyl-4-piperidine carboxylic acid and the hydrochloride salts thereof, sodium 1-[3,3-diphenyl-3-(2-pyridyl)propyl]-4-phenyl-4-piperidinecarboxylate; potassium 1-[3,3-diphenyl-3-(2-pyridyl) propyl]-4-phenyl-4-piperidinecarboxylate; ammonium 1-[3,3-diphenyl-3-(2-pyridyl)propyl]-4-phenyl-4-piperidinecarboxylate; ethyl 1-[3,3-diphenyl-3-(2-pyridyl)propyl]-4-phenyl-4-piperidinecarboxylate and the hydrochloride salts thereof.

Equivalent to acids and esters of this invention are the pharmaceutically acceptable acid addition salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Acids and esters of the present invention can be conveniently converted to ketones such as alkyl ketones having 1-10 carbon atoms or phenyl ketones wherein phenyl is Ar" as hereinbefore defined. The acids and esters may also be converted to amides such as N,N-dialkyl amides wherein the alkyl group has 1-7 carbon atoms or cycloalkylamides such as those derived from piperidine, piperazine, morpholine, and pyrrolidine by well recognized techniques.

Aldehydes corresonding to acids and esters of the present invention are likewise prepared by a variety of art recognized techniques. Amides, ketones, aldehydes have varying degrees of antidiarrheal activity.

Those skilled in the pharmaceutical arts also will recognize the equivalence of readily hydrolyzable esters which convert to the acids of the present invention upon administration to an animal such as succinimide esters.

Compounds of the present invention are prepared by

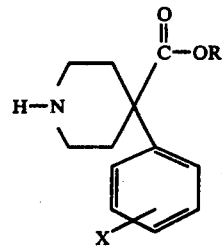

wherein R and X are defined as before in a suitable inert solvent such as toluene, benzene, methylene chloride, 4-methyl-2-pentanone or cyclohexane in the presence of an acid acceptor such as triethylamine or potassium carbonate to give the compounds of Formula I.

Resulting esters can be converted to other esters, acids or salts by recognized art techniques.

Compounds of the present invention are also prepared by methods set out in Scheme I

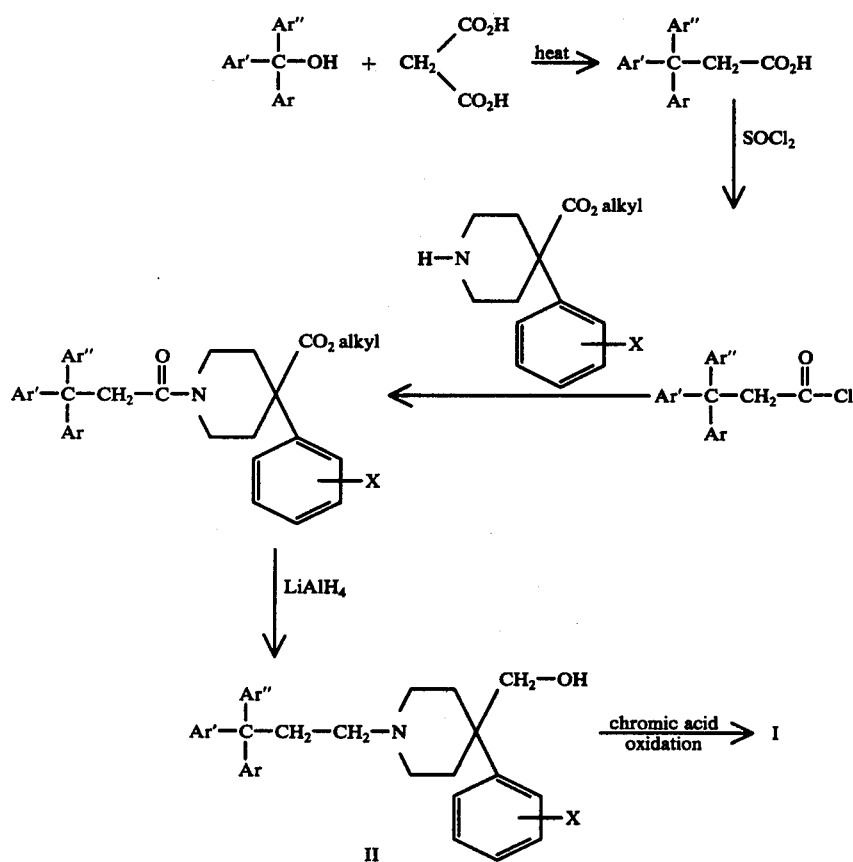

reacting a compound of the formula

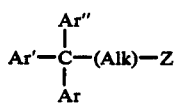

wherein Alk, Ar, Ar', Ar" are defined as before and Z is chlorine or bromine with a compound of the general formula wherein Ar, Ar', Ar" and X are as previously defined.

Oxidation of Compound II with chromic acid by modified procedure described in J. Clin Chem Soc 2498 (1964), conveniently provides compounds of the present invention.

Another process for the preparation of compounds of the present invention wherein R of Formula I is alkyl or alkanoyl comprises reacting a compound of the general formula

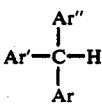

wherein Ar, Ar' and Ar" are defined as before with n-butyl lithium in a suitable organic solvent and further reacting this mixture with a compound of the general formula

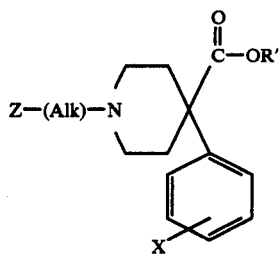

wherein Alk and X are defined as before and Z is chlorine or bromine and R' is alkyl or phenyl to give the compounds of Formula I wherein R is alkyl or phenyl.

Useful techniques and intermediates are disclosed by S. Patai and Dayogi, J. Chem Soc 716(1962), D. Martensson, E. Nilsson, Acta Chem Scand. 19(3) 711 (1965) CA-63-6968h and H. Bochow Chem Ber 108, 3475(1975) and U.S. Pat. No. 2,898,340. A wide variety of triphenylcarbinols are prepared by the reaction:

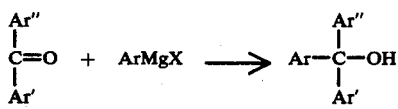

N-(3,3,3-triphenylpropyl)morpholine and N-(3,3,3-triphenylpropyl)piperidine are known compounds, Martensson and Nilsson, Acta Chem Scand 19 (1965) 711-722. Compounds of the present invention are particularly distinct by virtue of —$CO_2R$ and X substituted phenyls in the 4 position of the piperidine ring.

Compounds of the present invention are potent antidiarrheal agents with little, if any, central nervous system activity.

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil, olive oil, corn oil, oil of theobroma; water; agar; alginic acid; and benzyl alcohol, as well as other non-toxic compatible substances used in pharmaceutical formulations.

The compounds of this invention can be used to produce and antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particularly active ingredient is determined by comparing its potency to that of a known standard such as diphenoxylate HC1 (Cutting's Handbook of Pharmacology 4th edition, Appletoncentury Crafts, N.Y. at page 642).

Castor Oil Induced Diarrhea in the Rat

Adult Charles River male rats were fasted in community cages for 24 hours prior to the test, with free access to water. The compound was administered intragastrically (suspended on 0.5% methylcellulose) 1 hour prior to the administration of castor oil at the dose of 1.0 ml/rat intragastrically. The rats were then observed for the presence or absence of diarrhea, at hourly intervals for up to 8 hours past administration of castor oil. The median effective dose values at each hourly interval were calculated for the compound using the method of Berkson (1953). When tested in the above procedures 1-(3,3,3-triphenylpropyl)-4-phenyl-4-piperidinemethanol was found to be very active in its ability to inhibit gastrointestinal motility.

Charcoal Meal Test

Mice weighing 18–24 grams and previously fasted for 24 hours are each given orally 0.2 ml of a suspension containing 10% charcoal and 1% methylcellulose. The test compounds are administered intragastrically 1 hour prior to the charcoal meal. 3.5 Hours after administration of the meal the mice are sacrificed by cervical dislocation and the cecum is examined for the presence or absence of charcoal on an all-or-none basis. Each compound is tested at three dose levels (typically 30, 10, 3 mg/kg) in groups of 6 mice per dose level. Control groups of mice given vehicle only were run concurrently with each test group.

The assessment of the analgesic effect of the instant compounds was conducted in the mouse hot plate and tail clip tests.

Mouse Hot Plate Test

A mouse (adult male weighing 18–25 grams) is placed in a restraining cylinder on a hot plate with the temperature controlled at 55° ± 0.3° C. The reaction time of the mouse to lick a foot or jump is measured at 60, 40 and 20 minutes before and 30, 60, 90, and 120 minutes after administration of the test compound. The "normal" reaction time is measured as the median of the three pretreatment reaction times. A positive response consists of a reaction time greater than twice the normal time at any of the post treatment times. A dose of the test compound is considered active when 50 percent or more of the animals used show a positive response.

Tail Clip Test

A special clip is applied to the base of the tail of the mouse (adult male weighing 18–25 grams) and the time for the animal to turn around to bite at it is measured.

The sensitivity of each mouse is determined ½ hour prior to drug administration. Only those mice attempting to bite the clip are included in the experiment. The test compound is then administered and the response to placement of the clip is determined at 30, 60, 90, and 120 minutes after treatment. A response is considered positive if the animal takes more than 2 times the pre-drug time to bite at the clip at any of these time intervals. A test compound is considered active when 50 percent or more of the animals used show a positive response.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (° C), and relative amounts in parts by weight, except as otherwise noted.

EXAMPLE 1

A mixture of 9.9 parts of ethyl 4-phenyl-4-piperidinecarboxylate, 41.8 parts of 4-methyl-2-pentanone, 4.3 parts of ethylene oxide and 79.2 parts of ethanol is heated in a sealed citric bottle at about 60° C for 7 days. The resulting solution is cooled, the solvent is evaporated under reduced pressure and the residual material is partitioned between diluted NaOH and ether. The ether layer is then separated and extracted with diluted HCl. The acid layer is then made alkaline with aqueous sodium hydroxide and the resulting mixture is extracted with ether. The ether layer is dried over sodium sulfate and potassium carbonate and evaporated in vacuum. The residue is crystallized from ether-n-pentane to give ethyl 1-(2-hydroxyethyl)-4-phenyl-4-piperidinecarboxylate, melting at about 91.5°–93° C.

A solution is prepared from 5.9 parts of the ester obtained in the preceding paragraph and 134 parts of methylene chloride. This solution is saturated with hydrogen chloride gas at below 10° and 5.1 parts of thionyl chloride is added. The mixture is refluxed for 1 hour and then cooled and volatile material is removed under reduced pressure. The residue is dissolved in 88 parts of benzene, and the solution evaporated under reduced pressure. The residue is then crystallized from a mixture of ethanol and ether to give 1-(2-chloroethyl)-4-phenyl-4-piperidinecarboxylic acid ethyl ester hydrochloride melting at about 216°–218°.

To a solution of 4.4 parts of diphenyl-2-pyridylmethane in 50 parts of cyclohexane is added under nitrogen 8.8 parts by volume of a 2.17 molar solution of butyllithium in hexane. This solution is stirred at room temperature for 1.5 hours and then a solution of ethyl 1-(2-chloroethyl)-4-phenyl-4-piperidinecarboxylate, obtained from 6.0 parts of the corresponding hydrochloric salt, in 27 parts of cyclohexane is added and the mixture is refluxed with stirring for 4 hours. The mixture is cooled, diluted with 71 parts of ether and then washed with water. The organic layer is then extracted with dilute HCl resulting in the precipitation of gum. The aqueous layer is separated from the gum and the organic layer, washed with ether, made strongly alkaline with aqueous NaOH liberating brown-red oil, and extracted with ether. The ether extract is dried (Na$_2$SO$_4$) and evaporated under reduced pressure giving a brown-red gum. This gum is redissolved in ether, treated with Darco, filtered, concentrated and diluted with n-pentane for crystallization. This gives ethyl 1-[3,3-diphenyl-3-(2-pyridyl)propyl]-4-phenyl-4-piperidinecarboxylate melting at about 125°–128°. ED$_{50}$ (2 hrs. post castor oil) = 0.04 mpk and weak analgesia (mouse tail clip test) at 100 and 30 mpk. This compound has the following structural formula.

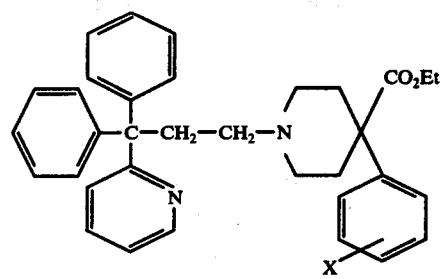

Hydrolysis of this ester in ethanolic sodium hydroxide is followed by removal of the ethanol, the addition of water and extraction of unreacted ester with ether. The pH of the aqueous layer is adjusted to 8.5 and air drying of the resulting precipitate provides 1-[3,3-diphenyl-3-(2-pyridyl)propyl]-4-phenyl-4-piperidine carboxylic acid melting at 270°–275° C. Treating the acid with sodium hydroxide, potassium hydroxide or ammonic hydroxide respectively provides sodium 1-[3,3-diphenyl-3-(2-pyridyl)propyl]-4-phenyl-4-piperidinecarboxylate; potassium 1-[3,3-diphenyl-3-(2-pyridyl)propyl]-4-phenyl-4-piperidinecarboxylate; or ammonium 1-[3,3-diphenyl-3-(2-pyridyl)propyl]-4-phenyl-4-piperidinecarboxylate.

EXAMPLE 2

A mixture of 63.7 parts of bis-2-chloroethylamine hydrochloride, 67.8 parts of 4-toluenesulphonyl chloride and 955 parts of methylene chloride is cooled in an ice bath and then 356 parts by volume of a 2 N aqueous sodium hydroxide solution is added with stirring at 5°–8° C. The mixture is stirred at 5°–8° C for 3 hours and then at room temperature for 18 hours. The organic layer is separated and washed successively with dilute hydrochloric acid, water, dilute potassium carbonate solution, and water and then dried over sodium sulfate. The solvent is then evaporated under reduced pressure and the residual oil is crystallized from methanol to give N,N-bis(2-chloroethyl)-4-toluenesulfonamide melting at about 45°–47° C.

To a solution of 60.3 parts of 4-chlorophenylacetonitrile and 118 parts of N,N-bis(2-chloroethyl)-4-toluenesulfonamide in 720 parts of dried benzene under N$_2$ there is added portionwise with stirring at 10°–13° C 32.6 parts of sodamide. The cooling bath is then removed and the mixture is stirred for 1 hour during which time the temperature rises to 70° C and then falls back to 43° C. Ice cold water is added to the mixture and a fine solid forms. This is separated by filtration and washed successively with water and benzene and dried and then triturated in boiling methanol. The undissolved solid is separated by filtration, washed with water and dried to give 1-(4-toluenesulfonyl)-4-(4-chlorophenyl)-4-piperidinecarbonitrile melting at about 202°–206° C.

The nitrile obtained in the preceding paragraph (37.5 parts) is added to 45.5 parts of 75% sulfuric acid with stirring. The resulting paste is heatedd to 140°–150° C with stirring for 1.5 hours. The mixture is then cooled and 120 parts of anhydrous ethanol is added. The mixture is then distilled until the pot temperature reaches 125° C. Addition of ethanol and distillation is repeated twice before the mixture is finally heated to 150° C and then cooled to room temperature. It is then poured into ice water containing excess sodium hydroxide. The mixture is then extracted with ether and the ether extract is dried and concentrated. It is then cooled to 0° C and filtered to remove solid material. The filtrate is then distilled to give a liquid boiling at 120°-125° C at 0.1 mm pressure. The distillate is then dissolved in 50 parts by volume of n-pentane and cooled to low temperature (−70° C) whereupon a gummy precipitate forms and the remaining liquid is removed by decantation; this is repeated four times and finally the gum solidifies. The solid is washed with cold pentane and then dried under reduced pressure to give 4-(4-chlorophenyl)-4-piperidinecarboxylic acid ethyl ester (an oil at room temperature).

A solution of 3.3 parts of 3,3,3-triphenylpropionic acid in 108 parts of dry benzene is treated with 1.8 parts of thionyl chloride. The mixture is refluxed for 2 hours before it is cooled and volatile material is removed under reduced pressure. The residue is dissolved in 88 parts of dry benzene and the solvent is removed again under reduced pressure to again give a residual oil. This is again dissolved in 88 parts of dry benzene and a solution of 2.9 parts of 4-(4-chlorophenyl)-4-piperidinecarboxylic acid ethyl ester and 1.1 part of triethylamine in 27 parts of dry benzene is added at 15°-25° C with stirring. The mixture is then allowed to stand for 16 hours before it is washed successively with dilute hydrochloric acid, water, and dilute aqueous potassium carbonate solution. It is then dried over sodium sulfate and the solvent is evaporated under reduced pressure to leave a residual gum. Upon trituration with pentane the gum solidifies and it is filtered, washed with pentane and air dried to give ethyl 1-(3,3,3-triphenylpropionyl)-4-(4-chlorophenyl)-4-piperidinecarboxylate, melting at about 95°-98° C. 3.8 Parts of this compound is continuously extracted into a suspension of 1.1 part of lithium aluminum hydride in ether with stirring at reflux under nitrogen over a period of 1 hour. Stirring is continued for an additional 50 minutes and the mixture is decomposed by the successive addition of 1.1 part of water, 0.8 part of 20% aqueous sodium hydroxide solution and 3.9 parts of water. The mixture is filtered and the inorganic material is extracted with ether. The combined ether solutions are concentrated and diluted with pentane. The solid material which forms is separated by filtration, washed with a mixture of ether and pentane, and dried under reduced pressure to give 1-(3,3,3-triphenylpropyl)-4-(4-chlorophenyl)-4-piperidinemethanol melting at about 156.5°-157.5° C and having the following structural formula.

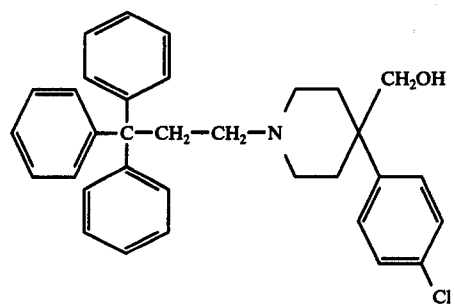

27.1 Parts of this alcohol is added to a solution of 8 parts by volume of sulfuric acid, 10 parts by volume of water and 53 parts by volume of acetic acid. To this mixture is added 24 parts by volume of a chromic acid solution made from 12.5 parts chromic acid in 12.5 parts by volume of water which is brought to 50 parts by volume with acetic acid over a 1.5 hour period. The reaction mixture is stirred for 18 hours and then heated on a steam bath for 1 hour. The reaction mixture is cooled and diluted with 100 parts water and made basic with sodium hydroxide. The intermediate aldehyde is removed by extracting the mixture with benzene and then the acid is isolated by adjusting the pH to 7.5 with aqueous hydrochloric acid and filtering the precipitate which is 1-(3,3,3-triphenylpropyl)-4-(4-chlorophenyl)-4-piperidinecarboxylic acid having the formula

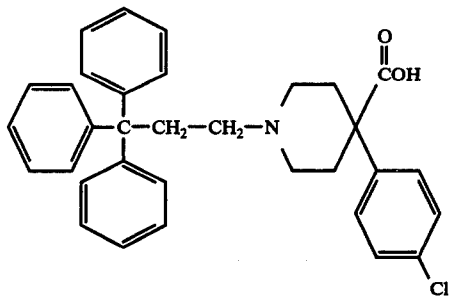

Substitution of p-tolylacetonitrile for 4-chlorophenyl acetonitrile used above and substantial repetition of the foregoing procedure provides 1-(3,3,3-triphenylpropyl)-4-(p-tolyl)-4-piperidinemethanol which in turn is converted to 1-(3,3,3-triphenylpropyl)-4-(p-tolyl)-4-piperidine carboxylic acid having the following structural formula

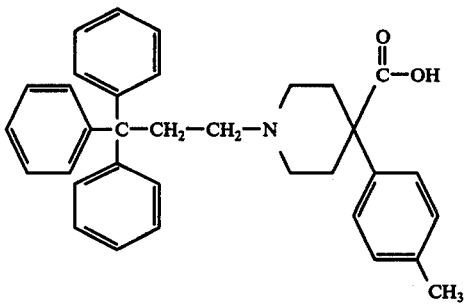

Substitution of 4-ethylphenylacetonitrile for 4-chlorophenylacetonitrile used above and substantial repetition of the foregoing procedure provides 1-(3,3,3- triphenylpropyl)-4-(p-ethylphenyl)-4-piperidinemethanol which in turn is converted to 1-(3,3,3-triphenylpropyl)-4-(p-ethylphenyl)-4-piperidine carboxylic acid having the formula

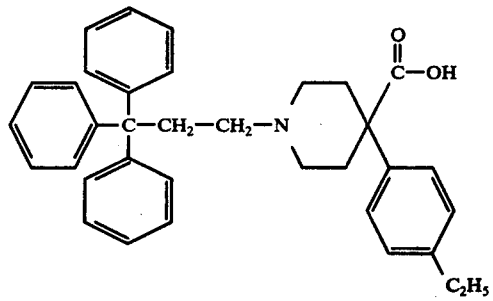

Substitution of p-fluorophenylacetonitrile for 4-chlorophenylacetonitrile used above and substantial repetition of the foregoing procedure provides 1-(3,3,3-triphenylpropyl)-4-(p-fluorophenyl)-4-piperidinemethanol which in turn is converted to 1-(3,3,3-triphenylpropyl)-4-(p-fluorophenyl)-4-piperidine carboxylic acid having the formula

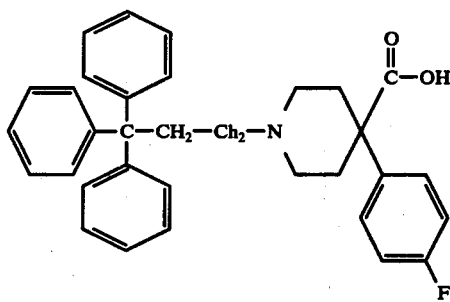

Substitution of p-trifluoromethylacetonitrile for 4-chlorophenylacetonitrile used above and substantial repetition of the foregoing procedure provides 1-(3,3,3-triphenylpropyl)-4-(p-trifluoromethylphenyl)-4-piperidinemethanol which in turn is converted to 1-(3,3,3-triphenyl-propyl)-4-(p-trifluoromethylphenyl)-4-piperidine carboxylic acid having the following structural formula

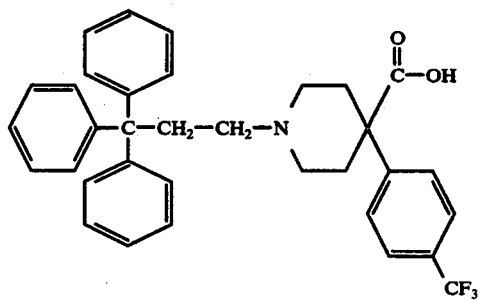

4,4,4-Triphenylbutyronitrile is hydrolyzed by standard procedure to give 4,4,4-triphenylbutyric acid. Substitution of 4,4,4-triphenylbutyric acid for the 3,3,3-triphenylpropionic acid of this example and substantial repetition of the procedure of Example 2 affords 1-(4,4,4-triphenylbutyl)-4-phenyl-4-piperidinemethanol which in turn is converted to 1-(4,4,4-triphenylbutyl)-4-phenyl-4-piperidinecarboxylic acid having the following structural formula

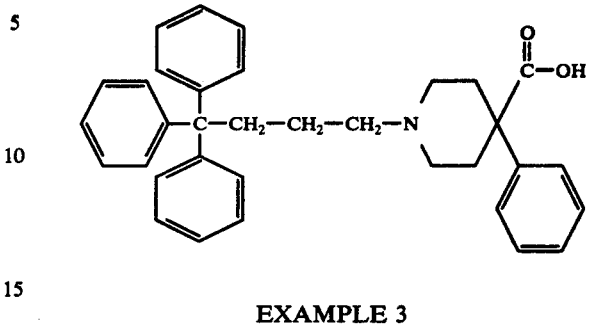

EXAMPLE 3

Following the procedure in Example 1 using 4.4 parts of diphenyl-3-pyridylmethane provides ethyl 1-[3,3-diphenyl-3-(3-pyridyl)propyl]-4-phenyl-4-piperidinecarboxylate having the formula

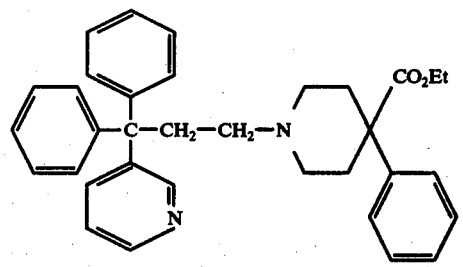

Also following methods of Example 1, ethyl is replaced with —CH$_3$, —CH$_2$—CH=CH$_2$, NH$_4$+, K+, or Ca++/2.

EXAMPLE 4

Following the procedure in Example 1 using 4.4 parts of diphenyl-4-pyridylmethane provides ethyl 1-[3,3-diphenyl-3-(4-pyridyl)propyl]-4-phenyl-4-piperidine carboxylate having the formula

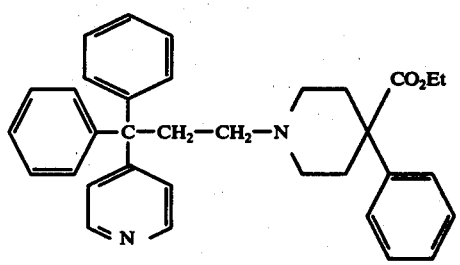

Also following methods of Example 1 ethyl is replaced with —CH$_3$, —CH$_2$—CH=CH$_2$, NH$_4$+, Na+, K+, or Ca++/2.

EXAMPLE 5

4.89 Parts of tetramethylethylenediamine and 2.33 parts of triphenylmethane are dissolved in 100 parts by volume of tetrahydrofuran and cooled to 10° C and kept under nitrogen and then 10.1 parts by volume of 2.17 molar n-butyl lithium is added. To the above reaction mixture is added 6.5 parts of ethyl 1-(2-chloroethyl)-4-phenyl-4-piperidino carboxylate in 50 parts by volume of tetrahydrofuran. The reaction is stirred for 1 hour and refluxed for 6 hours. The solvent is removed in vacuo and 250 parts by volume of ether is added followed by 100 parts by volume of water. The water is discarded and the ethereal layer is washed again with water. The ether is washed with 125 parts by volume of dilute hydrochloric acid and the resulting precipitate is filtered, dried, and recrystallized from 4:1 acetone/ether mixture to provide ethyl 1-(3,3,3-triphenylpropyl)-4-phenyl-4l-piperidinocarboxylate hydrochloride, melting at 205°-208° C and having the following structural formula

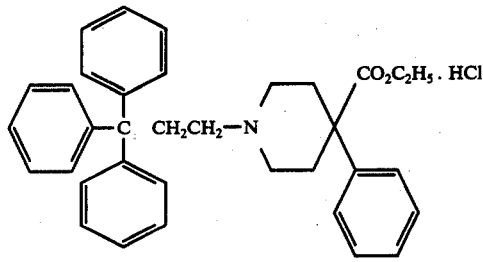

2.1 Parts of this ester salt and 1.38 parts of potassium hydroxide are dissolved in 100 parts by volume of ethanol and refluxed for 7.5 hours. The solvent is removed and the resulting potassium 1-(3,3,3-triphenylpropyl)-4-phenyl-4-piperidinecarboxylate is dissolved in hot water and after acidification, filtration of the solid, and recrystallization from toluene methanol provides (3,3,3-triphenylpropyl)-4-phenyl-4-piperidine carboxylic acid hydrochloride, melting at 256°-258° C and having the following formula

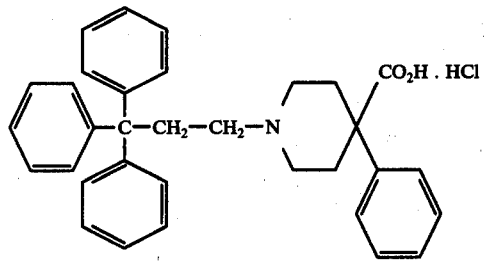

What is claimed is:
1. A compound of the formula

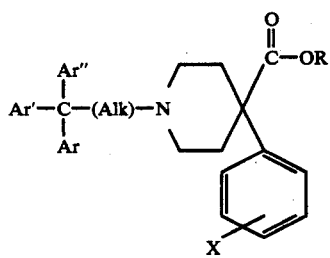

wherein the Alk is straight or branched chain alkylene containing 2-4 carbon atoms; Ar and Ar' are phenyl, alkyl substituted phenyl wherein the alkyl contains from 1-4 carbon atoms or halo substituted phenyl; Ar" is phenyl, alkyl substituted phenyl wherein the alkyl contains 1-4 carbon atoms, halo substituted phenyl or pyridyl; X is hydrogen, halogen, trifluoromethyl or alkyl having from 1-4 carbon atoms; R is hydrogen, alkyl having from 1-7 carbon atoms, alkenyl having 3-7 carbon atoms, Ar" as hereinbefore defined, or a cation selected from the group consisting of sodium, potassium, ammonium or calcium/2.

2. A compound according to claim 1 of the formula

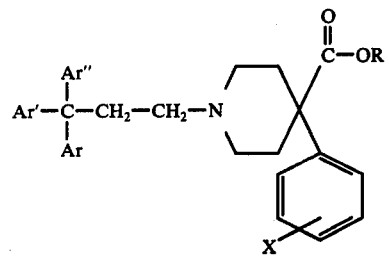

wherein Ar and Ar' are phenyl, alkyl substituted phenyl wherein the alkyl contains from 1-4 carbon atoms or halo substituted phenyl; Ar" is phenyl, alkyl substituted phenyl wherein the alkyl contains 1-4 carbon atoms, halo substituted phenyl or pyridyl; X is hydrogen, halogen, trifluoromethyl or alkyl having from 1-4 carbon atoms; R is hydrogen, alkyl having from 1-7 carbon atoms, Ar" as hereinbefore defined, or a cation selected from the group consisting of sodium, potassium, ammonium or calcium/2.

3. A compound according to claim 1 of the formula

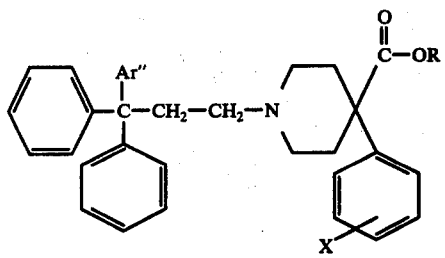

wherein Ar" is phenyl or pyridyl; X is hydrogen, halogen, trifluoromethyl or alkyl having from 1-4 carbon atoms; and R is hydrogen, alkyl having from 1-7 carbon atoms, or a cation selected from the group consisting of sodium, potassium, ammonium or calcium/2.

4. A compound according to claim 1 of the formula

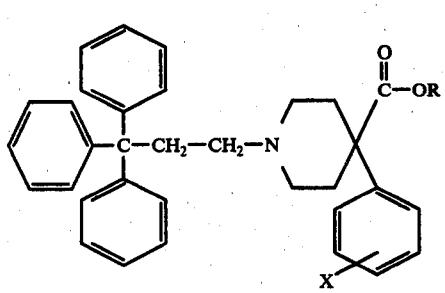

wherein X is hydrogen, halogen, trifluoromethyl or alkyl having from 1-4 carbon atoms; and R is hydrogen, alkyl having from 1-7 carbon atoms, or a cation selected from the group consisting of sodium, potassium, ammonium or calcium/2.

5. A compound according to claim 1 of the formula

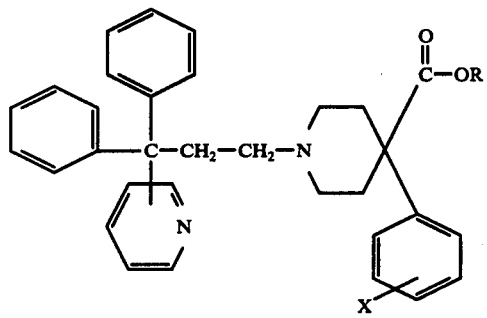

wherein X is hydrogen, halogen, trifluoromethyl or alkyl having from 1-4 carbon atoms; R is hydrogen, alkyl having from 1-7 carbon atoms, or a cation selected from the group consisting of sodium, potassium, ammonium or calcium/2.

6. A compound according to claim 1 which is 1(3,3,3-triphenylpropyl)-4-phenyl-4-piperidinecarboxylic acid hydrochloride.

7. A compound according to claim 1 which is ethyl 1-(3,3,3-triphenylpropyl)-4-phenyl-4-piperidinecarboxylate.

8. A compound according to claim 1 which is potassium 1-(3,3,3-triphenylpropyl)-4-phenyl-4-piperidinecarboxylate.

9. A compound according to claim 1 which is sodium 1-(3,3,3-triphenylpropyl)-4-phenyl-4-piperidinecarboxylate.

10. A compound according to claim 1 which is 1-[3,3-diphenyl-3-(2-pyridyl)propyl]-4-phenyl-4-piperidine carboxylic acid hydrochloride.

11. A compound according to claim 1 which is sodium 1-[3,3-diphenyl-3-(2-pyridyl)propyl]-4-phenyl-4-piperidinecarboxylate.

12. A compound according to claim 1 which is ethyl 1-[3,3-diphenyl-3-(2-pyridyl)propyl]-4-phenyl-4-piperidinecarboxylate.

13. A compound according to claim 1 which is potassium 1-[3,3-diphenyl-3-(2-pyridyl)propyl]-4-phenyl-4-piperidinecarboxylate.

* * * * *